United States Patent [19]

Förster et al.

[11] Patent Number: 5,356,864
[45] Date of Patent: Oct. 18, 1994

[54] NEW HERBICIDAL FLUOROBENZOTHIAZOLYLOXYACETAMIDES

[75] Inventors: Heinz Förster, Wuppertal; Klaus Wagner, Bergisch Gladbach; Hans-Joachim Santel, Leverkusen; Klaus Lürssen; Robert R. Schmidt, both of Bergisch Gladbach, all of Fed. Rep. of Germany

[73] Assignee: Bayer Aktiengesellschaft, Leverkusen, Fed. Rep. of Germany

[21] Appl. No.: 119,462

[22] Filed: Sep. 9, 1993

[30] Foreign Application Priority Data

Sep. 16, 1992 [DE] Fed. Rep. of Germany ....... 4230903

[51] Int. Cl.[5] ................ A01N 43/78; C07D 277/62
[52] U.S. Cl. .................................. 504/267; 548/171
[58] Field of Search ..................... 504/267; 548/171

[56] References Cited

U.S. PATENT DOCUMENTS

| 4,509,971 | 4/1985 | Förster et al. | 504/267 |
| 4,784,682 | 11/1988 | Förster et al. | 504/267 |
| 5,234,896 | 8/1993 | Wagner et al. | 504/267 |

FOREIGN PATENT DOCUMENTS 444764  2/1991  European Pat. Off. .

OTHER PUBLICATIONS

Chemical Abstracts, vol. 113, No. 3, Jul. 16, 1990, C. Paul Bianchi.

*Primary Examiner*—Richard L. Raymond
*Assistant Examiner*—Mary Cebulak
*Attorney, Agent, or Firm*—Sprung Horn Kramer & Woods

[57] ABSTRACT

Novel herbicidal fluorobenzothiazolyloxyacetamides of the formula

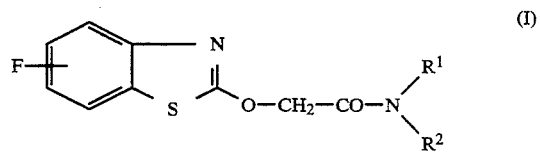

(I)

in which
R[1] represents hydrogen or an optionally substituted radical from the group consisting of alkyl, alkenyl, alkinyl and aralkyl,
R[2] represents an optionally substituted radical from the group consisting of alkyl, alkenyl, alkinyl, cycloalkyl, cycloalkenyl, aralkyl, aryl, alkoxy, alkenyloxy or alkinyloxy, or
R[1] and R[2], together with the nitrogen atom to which they are bonded, form an optionally substituted, saturated or unsaturated nitrogen heterocycle which can contain further heteroatoms and to which a benzo group can be fused.

14 Claims, No Drawings

NEW HERBICIDAL FLUOROBENZOTHIAZOLYLOXYACETAMIDES

The invention relates to new fluorobenzothiazolyloxyacetamides, to a process and new intermediates for their preparation and to their use as herbicides.

It has already been disclosed that certain benzothiazolyloxyacetamides, such as, for example, N-methylbenzothiazolyloxyacetanilide have herbicidal properties (cf. EP-A-5,501; U.S. Pat. Nos. 4,509,971, 4,784,682 and 4,833,243). However, the herbicidal activity of these known compounds is not always completely satisfactory.

New fluorobenzothiazolyloxyacetamides have now been found of the general formula (I)

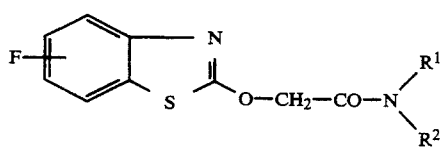

in which
$R^1$ represents hydrogen or an optionally substituted radical from the group consisting of alkyl, alkenyl, alkinyl and aralkyl,
$R^2$ represents an optionally substituted radical from the group consisting of alkyl, alkenyl, alkinyl, cycloalkyl, cycloalkenyl, aralkyl, aryl, alkoxy, alkenyloxy or alkinyloxy, or
$R^1$ and $R^2$, together with the nitrogen atom to which they are bonded, form an optionally substituted, saturated or unsaturated nitrogen heterocycle which can contain further heteroatoms and to which a benzo group can be fused.

It has further been found that the new fluorobenzothiazolyloxyacetamides of the formula (I) are obtained when fluorobenzothiazoles of the general formula (II)

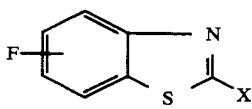

in which
X represents halogen or alkylsulphonyl,
are reacted with hydroxyacetamides of the general formula (III)

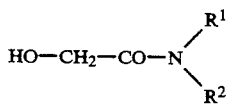

in which
$R^1$ and $R^2$ have the abovementioned meanings,
if appropriate in the presence of a diluent, if appropriate in the presence of an acid-binding agent and if appropriate in the presence of a catalyst.

Finally, it has been found that the new fluorobenzothiazolyloxyacetamides of the general formula (I) have interesting herbicidal properties.

Surprisingly, the compounds of the formula (I) according to the invention show, in some cases with very good tolerability to crop plants, such as, for example, rice, considerably stronger action against poorly controllable weeds, such as, for example, barnyard grass (Echinochloa crus galli) than the chemically similar known compound N-methylbenzothiazolyloxyacetanilide.

The invention preferably relates to compounds of the formula (I) in which
$R^1$ represents hydrogen, $C_1-C_8$-alkyl (which is optionally substituted by fluorine, chlorine, cyano or $C_1-C_4$-alkoxy), $C_2-C_8$-alkenyl (which is optionally substituted by fluorine and/or chlorine), $C_2-C_8$-alkinyl or benzyl,
$R^2$ represents $C_1-C_8$-alkyl (which is optionally substituted by fluorine, chlorine, cyano or $C_1-C_4$-alkoxy), $C_2-C_8$-alkenyl (which is optionally substituted by fluorine and/or chlorine), $C_2-C_8$-alkinyl, $C_3-C_6$-cycloalkyl (which is optionally substituted by chlorine and/or $C_1-C_3$-alkyl), $C_5$- or $C_6$-cycloalkenyl, benzyl (which is optionally substituted by fluorine, chlorine and/or $C_1-C_4$-alkyl), phenyl (which is optionally substituted by fluorine, chlorine, bromine, iodine, cyano, nitro, $C_1-C_4$-alkyl, trifluoromethyl, $C_1-C_4$-alkoxy and/or $C_1-C_4$-alkylthio), $C_1-C_8$-alkoxy (which is optionally substituted by $C_1-C_4$-alkoxy) or $C_3-C_4$-alkenyloxy, or
$R^1$ and $R^2$, together with the nitrogen atom to which they are bonded, form an optionally saturated or unsaturated five- to seven-membered nitrogen heterocycle which is monosubstituted to trisubstituted by $C_1-C_3$-alkyl and optionally benzo-fused.

The invention relates in particular to compounds of the formula (I) in which
$R^1$ represents $C_1-C_4$-alkyl, allyl or propargyl,
$R^2$ represents $C_1-C_6$-alkyl, $C_1-C_2$-alkoxy-$C_1-C_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy or ethoxy), $C_1-C_6$-alkoxy or $C_1-C_2$-alkoxy-$C_1-C_2$-alkoxy, or
$R^1$ and $R^2$, together with the nitrogen atom to which they are bonded, represent piperidinyl which is optionally monosubstituted to trisubstituted by methyl and/or ethyl, pyrrolidinyl which is optionally monosubstituted or disubstituted by methyl and/or ethyl, perhydroazepinyl or 1,2,3,4-tetrahydro(iso)quinolyl.

Very particularly preferred groups of compounds of the formula (I) are illustrated below by the formulae (IA), (IB), (IC) and (ID), where $R^1$ and $R^2$ have the meanings indicated above as preferred or as particularly preferred.

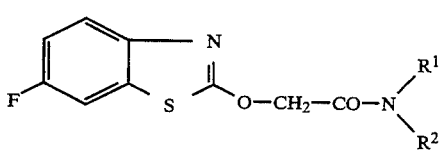

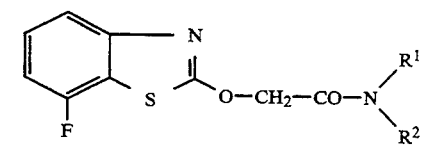

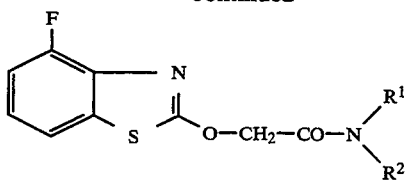  (IC)

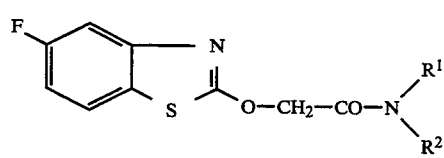  (ID)

The abovementioned definitions or explanations of radicals, which are general or mentioned in ranges of preference, correspondingly apply to the final products and to the starting materials and intermediates. These definitions of radicals can be combined with one another in any desired manner, i.e. also between the respective ranges of preference.

Examples of the possible meanings of the group

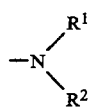

in the formulae (I), (IA), (IB), (IC) and (ID) are shown in Table 1 below.

TABLE 1

Examples of the meaning of the group 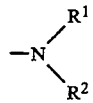

| 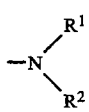 | 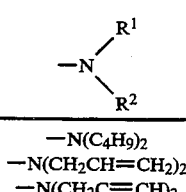 |
|---|---|
| —N(CH$_3$)$_2$ | —N(C$_4$H$_9$)$_2$ |
| —N(C$_2$H$_5$)$_2$ | —N(CH$_2$CH=CH$_2$)$_2$ |
| —N(C$_3$H$_7$)$_2$ | —N(CH$_2$C≡CH)$_2$ |
| 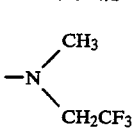 | 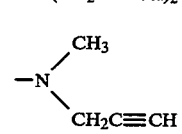 |
| 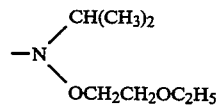 | 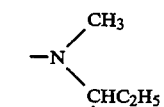 |
| 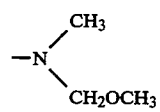 | 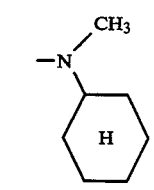 |

TABLE 1-continued

Examples of the meaning of the group 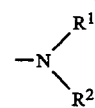

| 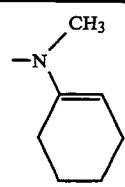 | 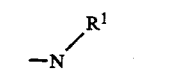 |
|---|---|
| 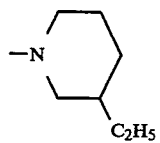 | 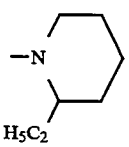 |
| 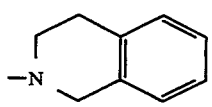 | 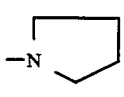 |
| 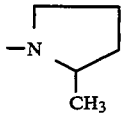 | 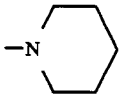 |
| 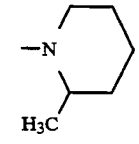 | 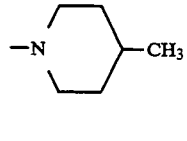 |
| 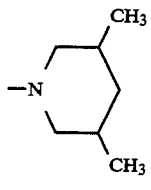 | 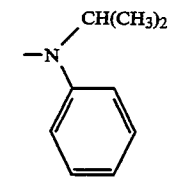 |
| | |
| 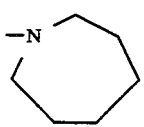 | 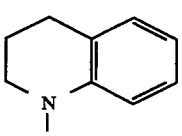 |

TABLE 1-continued

Examples of the meaning of the group $-N\begin{smallmatrix}R^1\\R^2\end{smallmatrix}$

| $-N\begin{smallmatrix}R^1\\R^2\end{smallmatrix}$ | $-N\begin{smallmatrix}R^1\\R^2\end{smallmatrix}$ |
|---|---|
| $-N(CH_3)(C_6H_5)$ | $-N(C_2H_5)(C_6H_5)$ |
| $-N(CH(CH_3)_2)(2\text{-}F\text{-}C_6H_4)$ | $-N(CH(CH_3)_2)(3\text{-}F\text{-}C_6H_4)$ |
| $-N(CH(CH_3)_2)(4\text{-}Cl\text{-}C_6H_4)$ | $-N(CH_3)(2\text{-}CH_3\text{-}C_6H_4)$ |
| $-N(CH(CH_3)_2)(4\text{-}CH_3\text{-}C_6H_4)$ | $-N(CH(CH_3)_2)(4\text{-}OCH_3\text{-}C_6H_4)$ |
| $-N(CH(CH_3)_2)(3\text{-}CH_3\text{-}C_6H_4)$ | $-N(CH(CH_3)_2)(4\text{-}CF_3\text{-}C_6H_4)$ |
| $-N(CH_3)(C_2H_5)$ | $-N(CH_3)(C_3H_7)$ |
| $-N(CH_3)(CH(CH_3)_2)$ | $-N(CH_3)(C_4H_9)$ |
| $-N(CH_3)(CH_2CH(CH_3)_2)$ | $-N(C_3H_7)(CHC_2H_5\text{-}CH_3)$ |
| $-N(C_2H_5)(C_3H_7)$ | $-N(C_2H_5)(CH(CH_3)_2)$ |
| $-N(C_2H_5)(C_4H_9)$ | $-N(C_2H_5)(CH_2CH(CH_3)_2)$ |
| $-N(C_2H_5)(CHC_2H_5\text{-}CH_3)$ | $-N(C_3H_7)(CH(CH_3)_2)$ |
| $-N(C_2H_5)(C_6H_{11})$ | $-N(C_3H_7)(C_6H_{11})$ |
| $-N(CH(CH_3)_2)(C_6H_{11})$ | $-N(CH_3)(CH_2C_6H_5)$ |
| $-N(C_2H_5)(CH_2C_6H_5)$ | $-N(C_3H_7)(CH_2C_6H_5)$ |
| $-N(CH(CH_3)_2)(CH_2C_6H_5)$ | $-N(CH_3)(CH_2\text{-}4\text{-}F\text{-}C_6H_4)$ |
| $-N(CH_3)(CH_2\text{-}4\text{-}Cl\text{-}C_6H_4)$ | $-N(CH_3)(CH_2\text{-}3\text{-}Cl\text{-}C_6H_4)$ |
| $-N(CH_3)(CH_2\text{-}2\text{-}Cl\text{-}C_6H_4)$ | $-N(C_2H_5)(CH_2\text{-}4\text{-}F\text{-}C_6H_4)$ |

TABLE 1-continued

Examples of the meaning of the group $$-N\begin{matrix}R^1\\R^2\end{matrix}$$

| $-N\begin{matrix}R^1\\R^2\end{matrix}$ | $-N\begin{matrix}R^1\\R^2\end{matrix}$ |
|---|---|
| $-N\begin{matrix}CH(CH_3)_2\\CH_2-C_6H_4-F(4)\end{matrix}$ | $-N\begin{matrix}C_2H_5\\CH_2-C_6H_4-Cl(4)\end{matrix}$ |
| $-N\begin{matrix}CH(CH_3)_2\\CH_2-C_6H_4-Cl(4)\end{matrix}$ | $-N\begin{matrix}CH_3\\C_6H_4-F(4)\end{matrix}$ |
| $-N\begin{matrix}C_2H_5\\C_6H_4-F(4)\end{matrix}$ | $-N\begin{matrix}CH_3\\C_6H_4-Cl(4)\end{matrix}$ |
| $-N\begin{matrix}C_2H_5\\C_6H_4-Cl(4)\end{matrix}$ | $-N\begin{matrix}CH_3\\C_6H_3-2-CH_3-3-Cl\end{matrix}$ |
| $-N\begin{matrix}CH_3\\C_6H_3-3-Cl-4-F\end{matrix}$ | $-N\begin{matrix}CH_3\\C_6H_3-3,4-F_2\end{matrix}$ |
| $-N\begin{matrix}CH(CH_3)_2\\C_6H_3-3,4-F_2\end{matrix}$ | $-N\begin{matrix}CH(CH_3)_2\\C_6H_3-3-Cl-4-F\end{matrix}$ |
| $-N\begin{matrix}CH_3\\C_6H_3-2,4-F_2\end{matrix}$ | $-N\begin{matrix}CH(CH_3)_2\\C_6H_3-2,4-F_2\end{matrix}$ |
| $-N\begin{matrix}CH_3\\C_6H_3-3,5-(CH_3)_2\end{matrix}$ | $-N\begin{matrix}CH(CH_3)_2\\C_6H_4-4-CF_3\end{matrix}$ |
| $-N\begin{matrix}CH_3\\C_6H_4-3-CF_3\end{matrix}$ | $-N\begin{matrix}CH_3\\C_6H_3-3,5-(CF_3)_2\end{matrix}$ |
| $-N\begin{matrix}CH_3\\C_6H_3-2,4-(CH_3)_2\end{matrix}$ | $-N\begin{matrix}CH(CH_3)_2\\C_6H_3-3,5-F_2\end{matrix}$ |
| $-N\begin{matrix}CH(CH_3)_2\\C_6H_3-3,4-Cl_2\end{matrix}$ | $-N\begin{matrix}CH(CH_3)_2\\C_6H_3-3,4-(CH_3)_2\end{matrix}$ |
| $-N\begin{matrix}CH_3\\C_6H_3-3,5-Cl_2\end{matrix}$ | $-N\begin{matrix}CH_3\\CH_2CH_2CN\end{matrix}$ |
| $-N\begin{matrix}C_2H_5\\CH_2CH_2CN\end{matrix}$ | $-N(CH_2CH_2CN)_2$ |

TABLE 1-continued

Examples of the meaning of the group $$-N\begin{matrix}R^1\\R^2\end{matrix}$$

| $-N\begin{matrix}R^1\\R^2\end{matrix}$ | $-N\begin{matrix}R^1\\R^2\end{matrix}$ |
|---|---|
| $-N\begin{matrix}CH(CH_3)_2\\CH_2CH_2OCH_3\end{matrix}$ | $-N\begin{matrix}C_2H_5\\CH_2CH_2OCH_3\end{matrix}$ |
| $-N\begin{matrix}CH_3\\CH_2CH_2OCH_3\end{matrix}$ | $-N\begin{matrix}CH_3\\OC_2H_5\end{matrix}$ |
| $-N\begin{matrix}CH_3\\OC_3H_7\end{matrix}$ | $-N\begin{matrix}CH_3\\OC_4H_9\end{matrix}$ |
| $-N\begin{matrix}C_2H_5\\OC_2H_5\end{matrix}$ | $-N\begin{matrix}C_2H_5\\OC_3H_7\end{matrix}$ |
| $-N\begin{matrix}C_2H_5\\OC_4H_9\end{matrix}$ | $-N\begin{matrix}C_3H_7\\OC_3H_7\end{matrix}$ |
| $-N\begin{matrix}C_3H_7\\OC_4H_9\end{matrix}$ | $-N\begin{matrix}CH(CH_3)_2\\OC_2H_5\end{matrix}$ |
| $-N\begin{matrix}CH(CH_3)_2\\OC_3H_7\end{matrix}$ | $-N\begin{matrix}CH(CH_3)_2\\OCH_2CH_2OCH_3\end{matrix}$ |
| $-N\begin{matrix}CH_3\\\text{3-Cl-C}_6H_4\end{matrix}$ | $-N\begin{matrix}CH_3\\\text{4-CH}_3\text{-C}_6H_4\end{matrix}$ |
| $-N\begin{matrix}CH(CH_3)_2\\\text{3-Cl-C}_6H_4\end{matrix}$ | $-N\begin{matrix}C_3H_7\text{-n}\\OCH(CH_3)_2\end{matrix}$ |
| $-N\begin{matrix}CH(CH_3)_2\\\text{4-CH}_3\text{-C}_6H_4\end{matrix}$ | |

If, for example, 2-chloro-6-fluoro-benzothiazole and N,N-diethyl-hydroxyacetamide are used as starting substances, the course of the reaction in the preparation process according to the invention can be represented by the following reaction scheme:

[4-fluoro-2-chlorobenzothiazole structure] +

HO—CH$_2$—CO—N(C$_2$H$_5$)$_2$ $\xrightarrow{-HCl}$

[4-fluoro-benzothiazole-2-O—CH$_2$—CO—N(C$_2$H$_5$)$_2$ structure]

Formula (II) provides a general definition of the fluorobenzothiazoles to be used as starting substances in the process according to the invention for the preparation of the compounds of the formula (I).

In formula (II), X preferably represents fluorine, chlorine or bromine as well as C$_1$–C$_4$-alkylsulphonyl, in particular chlorine or methylsulphonyl.

With the exception of 2,6-difluoro-benzothiazole and 2-chloro-6-fluoro-benzothiazole (cf. Org. Magn. Reson. 7 (1975), 84–85—cited in Chem. Abstracts 83:113186x), the starting substances of the formula (II) are not yet known from the literature and, with the exception of the two known compounds mentioned, are—as new substances—also a subject of the present invention.

Examples of the new compounds of the formula (II) which may be mentioned are:

2-Chloro-4-fluoro-benzothiazole, 2-chloro-5-fluoro-benzothiazole, 2-chloro-7-fluoro-benzothiazole, 2-methyl-sulphonyl-4-fluoro-benzothiazole, 2-methylsulphonyl-5-fluoro-benzothiazole, 2-methylsulphonyl-6-fluoro-benzothiazole and 2-methylsulphonyl-7-fluoro-benzothiazole.

The fluorobenzothiazoles of the general formula (II) are obtained when (a) in the case in which X represents halogen, 2-amino-fluorobenzothiazoles of the general formula (IV)

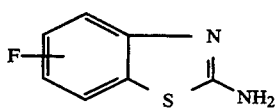

(IV)

are reacted with diazotising and halogenating agents, such as, for example, sodium nitrite, hydrochloric acid and copper powder, at temperatures between −10° C. and +60° C. (cf. the preparation examples).

The 2-amino-fluorobenzothiazoles of the formula (IV) are known and/or can be prepared by processes known per se (cf. J. Chem. Soc. C 1969, 268–272; J. Heterocycl. Chem. 18 (1981), 759–761; Synthet. Commun. 17 (1987), 229–240; EP-A 282971; preparation examples).

The fluorobenzothiazoles of the formula (II) are also obtained when (b) in the case in which X represents halogen, 2-mercapto-fluorobenzothiazoles of the general formula (V)

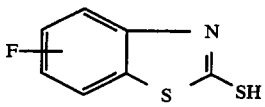

(V)

are reacted with halogenating agents, such as, for example, thionyl chloride, if appropriate in the presence of reaction auxiliaries, such as, for example, dimethylformamide, at temperatures between 0° C. and 100° C. (cf. the preparation examples), or when (c) in the case in which X represents alkylsulphonyl, 2-mercapto-fluorobenzothiazoles of the formula (V) are reacted with alkylating agents, such as, for example, methyl iodide, if appropriate in the presence of acid-binding agents, such as, for example, sodium hydroxide and in the presence of diluents, such as, for example, water, at temperatures between −10° C. and +100° C. and the alkylation products obtained in this way are reacted with oxidising agents, such as, for example, hydrogen peroxide, if appropriate in the presence of reaction auxiliaries, such as, for example, formic acid, sulphuric acid and ammonium molybdate, at temperatures between 0° C. and 50° C. (cf. the preparation examples).

The 2-mercapto-fluorobenzothiazoles of the formula (V) are known and/or can be prepared by processes which are known per se (cf. DE-OS (German Published Specification) 3,008,225; U.S. Pat. No. 4,873,346; preparation examples).

Formula (III) provides a general definition of the hydroxyacetamides further to be used as starting substances in the process according to the invention for the preparation of compounds of the formula (I).

In formula (III), $R^1$ and $R^2$ preferably or in particular have those meanings which have already been indicated above as preferred or as particularly preferred for $R^1$ and $R^2$ in connection with the description of the compounds of the formula (I) according to the invention.

The hydroxyacetamides of the formula (III) are known and/or can be prepared by processes known per se (cf. U.S. Pat. Nos. 4,509,971 and 4,645,525; also U.S. Pat. No. 4,334,073, DE-OS (German Published Specification) 3,038,598, DE-OS (German Published Specification) 3,038,636, EP-A-37,526, EP-A-348,737 and DE-OS (German Published Specification) 3,819,477).

The process according to the invention for the preparation of the new fluorobenzothiazolyloxyacetamides of the formula (I) is preferably carried out using diluents. These preferably include hydrocarbons, such as, for example, toluene, xylene or cyclohexane, halogenohydrocarbons, such as, for example, methylene chloride, ethylene chloride, chloroform or chlorobenzene, ethers, such as, for example, diethyl ether, dipropyl ether, diisopropyl ether, dibutyl ether, diisobutyl ether, glycol dimethyl ether, tetrahydrofuran and dioxane, alcohols, such as, for example, methanol, ethanol, propanol, isopropanol, butanol, isobutanol, sec-butanol or tert-butanol, ketones, such as, for example, acetone, methyl ethyl ketone, methyl isopropyl ketone and methyl isobutyl ketone, esters, such as, for example, methyl acetate and ethyl acetate, amides, such as, for example, dimethylformamide, dimethylacetamide, and N-methyl-pyrrolidone, nitriles, such as, for example, acetonitrile and propionitrile, sulphoxides, such as, for example, dimethyl sulphoxide and also water or aqueous salt solutions.

The salts used here are preferably chlorides or sulphates of alkali metals or alkaline earth metals, such as, for example, sodium chloride, potassium chloride or calcium chloride. Sodium chloride is particularly preferred.

The process according to the invention is advantageously carried out using acid-binding agents. Those which are preferably used are strongly basic alkali metal and alkaline earth metal compounds, for example oxides, such as, for example, sodium oxide, potassium oxide, magnesium oxide and calcium oxide, hydroxides, such as, for example, sodium hydroxide, potassium hydroxide, magnesium hydroxide and calcium hydroxide, alkoxides, such as, for example, sodium tert-butoxide and potassium tert-butoxide and/or carbonates, such as, for example, sodium carbonate, potassium carbonate, magnesium carbonate and calcium carbonate.

The addition of 0.01 to 10% by weight (relative to glycolic acid amide of the formula (III) employed of a phase transfer catalyst may in some cases prove advantageous. Examples of such catalysts which may be mentioned are:

Tetrabutylammonium chloride, tetrabutylammonium bromide, tributyl-methylphosphonium bromide, trimethyl-$C_{13}/C_{15}$-alkyl-ammonium chloride, dibenzyl-d ethyl-ammonium methylsulphate, dimethyl-$C_{12}/C_{14}$-alkyl-benzylammonium chloride, tetrabutylammonium hydroxide, 18-crown-6, triethylbenzylammoniumchloride, trimethylbenzylammonium chloride, tetraethylammonium bromide.

The reaction temperatures in the process/according to the invention can be varied within a relatively wide range. In general, the reaction is carried out at temperatures between −50° C. and +110° C., preferably at temperatures between −20° C. and +80° C.

The process according to the invention is in general carried out at normal pressure, but it can also be carried out at elevated or reduced pressure, for example between 0.1 and 10 bar.

To carry out the process according to the invention, 0.5 to 5 mol, preferably 0.8 to 1.5 mol, of hydroxyacetamide of the formula (III) are in general employed per mole of fluorobenzothiazole of the formula (II). The reaction components can be mixed together in any desired sequence. The reaction mixture is in each case stirred until the end of the reaction and worked up according to customary methods (cf. the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending or the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture land, and for the selective combating of weeds in annual cultures.

The compounds of the formula (I) according to the invention are particularly suitable for the selective control of monocotyledon weeds, such as, for example, barnyard grass (*Echinochloa crus galli*) in transplanted rice. However, they can also be employed generally for the control of monocotyledon weeds in dicotyledon crop plants populations.

The active compounds can be converted into the customary formulations, such as solutions, emulsions, suspensions, powders, foes, pastes, granules, aerosols, natural and synthetic materials impregnated with active compound, and very fine capsules in polymeric substances.

These formulations are produced in a known manner, for example by mixing the active compounds with extenders, that is liquid solvents, liquified gases under pressure and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ether: and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foamforming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as organic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES:

Example 1

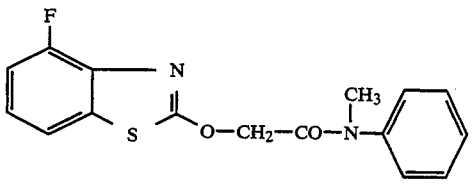

A solution of 0.6 g (15 mmol) of sodium hydroxide in 2.7 ml of water is added dropwise with stirring at 20° C. to a mixture of 2.5 g (15 mmol) of N-methyl-hydroxyacetanilide, 3.5 g (15 mmol) of 2-methylsulphonyl-4-fluoro-benzothiazole and 50 ml of acetone. The reaction mixture is stirred at 20° C. for 12 hours and then poured into about twice the volume of water. The product obtained in crystalline form in this way is isolated by filtering off with suction.

3.8 g (79% of theory) of N-methyl-α-(4-fluoro-benzothiazol-2-yl-oxy)-acetanilide of melting point 94° C. are obtained.

Example 2

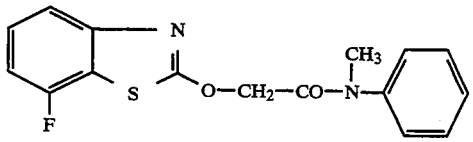

A solution of 3.75 g (16.6 mmol) of 2-chloro-7-fluoro-benzothiazole in 20 ml of acetonitrile is added dropwise with stirring to a mixture, cooled to −10° C., of 2.74 g (16.6 mmol) of N-methyl-hydroxyacetanilide, 0.93 g (16.6 mmol) of potassium hydroxide and 50 ml of isopropanol. The reaction mixture is stirred at 0° C. to 5° C. for 6 hours, then poured into about twice the volume of water and extracted three times with methylene chloride. The combined organic phases are washed with water, dried with sodium sulphate and filtered. After concentration of the filtrate, the residue is purified by column chromatography two times (1. silica gel/methylene chloride, 2. silica gel/methyl tert-butyl ether).

1.4 g (27% of theory) of N-methyl-α-(7-fluoro-benzothiazol-2-yl-oxy)-acetanilide of melting point 116° C. are obtained.

The compounds of the formula (I):

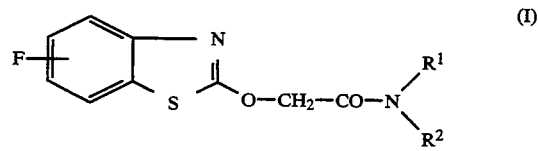

(I)

shown in Table 2 below can also be prepared, for example, analogously to Examples 1 and 2 and corresponding to the general description of the preparation process according to the invention.

TABLE 2

Preparation Examples of the compounds of the formula (I)

| Ex. No. | Position of F | $R^1$ | $R^2$ | Melting point (°C.) (refractive index) |
|---|---|---|---|---|
| 3 | 5 | $CH_3$ | 2,6-dimethylphenyl | 144 |
| 4 | 5 | $CH(CH_3)_2$ | 4-fluorophenyl | 115 |
| 5 | 5 | $CH(CH_3)_2$ | phenyl | 113 |
| 6 | 5 | $CH_3$ | 3-methylphenyl | 115 |
| 7 | 5 | $CH_3$ | 2-methylphenyl | 146 |
| 8 | 5 | \multicolumn{2}{c}{$-(CH_2)_6-$} | 114 |
| 9 | 5 | $C_2H_5$ | phenyl | 97 |
| 10 | 5 | $CH_3$ | $n\text{-}C_4H_9$ | 53 |
| 11 | 5 | $-CH_2CH=CH_2$ | $-CH_2CH=CH_2$ | ($n_D^{20}$: 1.5345) |
| 12 | 5 | $CH_3$ | phenyl | 92 |
| 13 | 6 | $CH(CH_3)_2$ | 4-fluorophenyl | 72 |
| 14 | 6 | $CH(CH_3)_2$ | phenyl | 108 |
| 15 | 6 | $CH_3$ | 3-methylphenyl | 83 |
| 16 | 6 | $C_2H_5$ | $C_2H_5$ | 65 |
| 17 | 6 | | $-CH(CH_3)-(CH_2)_5-$ | ($n_D^{20}$: 1.5510) |
| 18 | 6 | $CH(CH_3)_2$ | $-OC_2H_4OC_2H_5$ | ($n_D^{20}$: 1.5128) |
| 19 | 6 | | $-(CH_2)_6-$ | 55 |
| 20 | 6 | $CH(CH_3)_2$ | $-OCH(CH_3)_2$ | 46 |
| 21 | 6 | $-CH_2CH=CH_2$ | $-CH_2CH=CH_2$ | 68 |
| 22 | 6 | $CH_3$ | $-CH(CH_3)-C_2H_5$ | 69 |

TABLE 2-continued

Preparation Examples of the compounds of the formula (I)

| Ex. No. | Position of F | R$^1$ | R$^2$ | Melting point (°C.) (refractive index) |
|---|---|---|---|---|
| 23 | 6 | \multicolumn{2}{c}{$(-N\overset{R^1}{\underset{R^2}{\diagdown}}\ :\ -N\diagdown)$ fused to tetrahydroquinoline} | 89 |
| 24 | 6 | n-C$_4$H$_9$ | n-C$_4$H$_9$ | (n$_D^{20}$: 1.5321) |
| 25 | 6 | CH$_3$ | n-C$_4$H$_9$ | 66 |
| 26 | 6 | CH(CH$_3$)$_2$ | —C$_6$H$_4$-OCH$_3$ (meta) | 86 |
| 27 | 5 | CH(CH$_3$)$_2$ | —C$_6$H$_4$-CH$_3$ (meta) | 125 |
| 28 | 5 | \multicolumn{2}{c}{$(-N\overset{R^1}{\underset{R^2}{\diagdown}}\ :\ -N\diagdown)$ fused to tetrahydroquinoline} | 128 |
| 29 | 7 | CH(CH$_3$)$_2$ | —C$_6$H$_5$ | 107 |
| 30 | 5 | CH(CH$_3$)$_2$ | —OCH(CH$_3$)$_2$ | (n$_D^{20}$: 1.5372) |
| 31 | 5 | —CH(CH$_3$)$_2$ | —OC$_2$H$_4$OC$_2$H$_5$ | (n$_D^{20}$: 1.5365) |
| 32 | 5 | \multicolumn{2}{c}{—CH$_2$—CH(CH$_3$)—(CH$_2$)$_3$—} | 64 |
| 33 | 4 | CH(CH$_3$)$_2$ | —C$_6$H$_5$ | 92 |
| 34 | 4 | CH(CH$_3$)$_2$ | —C$_6$H$_4$-F (para) | 76 |
| 35 | 4 | CH$_3$ | —C$_6$H$_4$-CH$_3$ (ortho) | 145 |
| 36 | 4 | CH$_3$ | —C$_6$H$_4$-CH$_3$ (meta) | 86 |
| 37 | 4 | —CH$_2$CH=CH$_2$ | —CH$_2$CH=CH$_2$ | 56 |

TABLE 2-continued

Preparation Examples of the compounds of the formula (I)

| Ex. No. | Position of F | R¹ | R² | Melting point (°C.) (refractive index) |
|---|---|---|---|---|
| 38 | 4 | —CH(CH$_3$)$_2$ | —OC$_2$H$_4$OC$_2$H$_5$ | (n$_D^{20}$: 1.4991) |
| 39 | 7 | —CH(CH$_3$)$_2$ |  —C$_6$H$_4$—F (para) | 108 |
| 40 | 7 | CH(CH$_3$)$_2$ | —OC$_2$H$_4$OC$_2$H$_5$ | 46 |
| 41 | 7 | CH(CH$_3$)$_2$ | —OCH(CH$_3$)$_2$ | 41 |
| 42 | 7 | CH$_3$ | 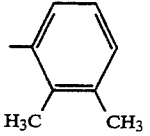 2,3-(CH$_3$)$_2$-C$_6$H$_3$— | 121 |
| 43 | 7 | CH$_3$ | 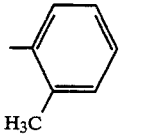 2-CH$_3$-C$_6$H$_4$— | 104 |
| 44 | 7 | CH$_3$ | n-C$_4$H$_9$ | 61 |
| 45 | 7 | —(CH$_2$)$_6$— | | 88 |
| 46 | 7 | CH$_3$ | 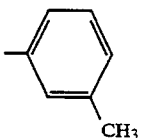 3-CH$_3$-C$_6$H$_4$— | 99 |
| 47 | 7 | CH(CH$_3$)$_2$ | 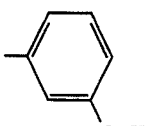 3-OCH$_3$-C$_6$H$_4$— | 113 |
| 48 | 7 | —CH$_2$CH=CH$_2$ | —CH$_2$CH=CH$_2$ | 56 |
| 49 | 5 | CH$_3$ | —CH(CH$_3$)—C$_2$H$_5$ | (n$_D^{20}$: 1.5305) |
| 50 | 5 | CH(CH$_3$)$_2$ | n-C$_6$H$_{13}$ | (n$_D^{20}$: 1.5208) |
| 51 | 5 | CH(CH$_3$)$_2$ | —CH$_2$CH$_2$CH(CH$_3$)$_2$ | (n$_D^{20}$: 1.5035) |
| 52 | 5 | C$_2$H$_5$ | C$_2$H$_5$ | (n$_D^{20}$: 1.5395) |
| 53 | 5 | —CH$_2$—CH(C$_2$H$_5$)—(CH$_2$)$_3$— | | (n$_D^{20}$: 1.5465) |
| 54 | 5 | CH(CH$_3$)$_2$ | 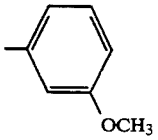 4-OCH$_3$-C$_6$H$_4$— | 102 |
| 55 | 5 | n-C$_4$H$_9$ | n-C$_4$H$_9$ | 42 |
| 56 | 5 | n-C$_3$H$_7$ | n-C$_3$H$_7$ | 60 |
| 57 | 5 | —CH(CH$_3$)—(CH$_2$)$_4$— | | 96 |
| 58 | 4 | CH(CH$_3$)$_2$ | 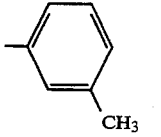 3-CH$_3$-C$_6$H$_4$— | 138 |
| 59 | 4 | CH(CH$_3$)$_2$ | —OCH(CH$_3$)$_2$ | 52 |
| 60 | 4 | n-C$_4$H$_9$ | n-C$_4$H$_9$ | 34 |
| 61 | 4 | —(CH$_2$)$_6$— | | 75 |
| 62 | 4 | —CH$_2$—CH(C$_2$H$_5$)—(CH$_2$)$_3$— | | (n$_D^{20}$: 1.5032) |
| 63 | 4 | CH$_3$ | —CH(CH$_3$)—C$_2$H$_5$ | 72 |

TABLE 2-continued

Preparation Examples of the compounds of the formula (I)

| Ex. No. | Position of F | R¹ | R² | Melting point (°C.) (refractive index) |
|---|---|---|---|---|
| 64 | 4 | n-C$_3$H$_7$ | n-C$_3$H$_7$ | 49 |
| 65 | 4 |  | —CH(CH$_3$)—(CH$_2$)$_4$— | 67 |
| 66 | 4 | C$_2$H$_5$ | C$_2$H$_5$ | 73 |
| 67 | 4 | C$_2$H$_5$ | ![phenyl] | 100 |
| 68 | 6 | CH$_3$ | 2-methylphenyl (H$_3$C) | 113 |
| 69 | 5 | CH(CH$_3$)$_2$ | —CH$_2$CH(CH$_3$)—CH(CH$_3$)—C$_2$H$_5$ | (n$_D$$^{20}$: 1.5246) |
| 70 | 5 | n-C$_3$H$_7$ | —CH$_2$CH(C$_2$H$_5$)$_2$ | (n$_D$$^{20}$: 1.5132) |
| 71 | 6 | CH$_3$ | 2,3-dimethylphenyl (H$_3$C, CH$_3$) | 148 |
| 72 | 6 |  | —CH$_2$—CH(C$_2$H$_5$)—(CH$_2$)$_3$— | (n$_D$$^{20}$: 1.5088) |
| 73 | 6 | n-C$_3$H$_7$ | n-C$_3$H$_7$ | (n$_D$$^{20}$: 1.5391) |
| 74 | 7 | n-C$_4$H$_9$ | n-C$_4$H$_9$ | (n$_D$$^{20}$: 1.5095) |
| 75 | 7 | CH(CH$_3$)$_2$ | 3-methylphenyl (CH$_3$) | 84 |
| 76 | 7 | n-C$_3$H$_7$ | n-C$_3$H$_7$ | 70 |
| 77 | 7 |  | —CH(CH$_3$)—(CH$_2$)$_4$— | 88 |
| 78 | 7 | CH$_3$ | —CH(CH$_3$)—C$_2$H$_5$ | 49 |
| 79 | 7 | C$_2$H$_5$ | phenyl | 92 |
| 80 | 6 | C$_2$H$_5$ | phenyl | 107 |
| 81 | 7 |  | —CH$_2$—CH(C$_2$H$_5$)—(CH$_2$)$_3$— | 60 |
| 82 | 7 | C$_2$H$_5$ | C$_2$H$_5$ | 45 |
| 83 | 4 | CH$_3$ | 4-fluorophenyl | 84 |
| 84 | 5 | CH$_3$ | 4-fluorophenyl | 85 |
| 85 | 7 | CH$_3$ | 4-fluorophenyl | 96 |

TABLE 2-continued

Preparation Examples of the compounds of the formula (I)

| Ex. No. | Position of F | R¹ | R² | Melting point (°C.) (refractive index) |
|---|---|---|---|---|
| 86 | 4 | C₂H₅ | —⟨C₆H₄⟩—F | 107 |
| 87 | 7 | C₂H₅ | —⟨C₆H₄⟩—F | 119 |
| 88 | 5 | C₂H₅ | —⟨C₆H₄⟩—F | 116 |

Starting substances of the formula (II)

Example (II-1)

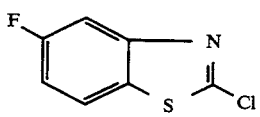

Step 1

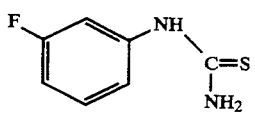

A mixture of 300 g (2.67 mol) of 3-fluoro-aniline, 271 g (2.67 mol) of conc. hydrochloric acid and 259 g (2.67 mol) of potassium thiocyanate is heated under reflux for 6 hours. After cooling, the product, which is obtained in crystalline form, is isolated by filtering off with suction.

190 g (41.5% of theory) of N-(3-fluoro-phenyl)-thiourea of melting point 109° C. are obtained.

Step 2

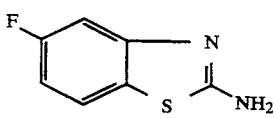

A solution of 176 g (1.1 mol) of bromine in 190 ml of chloroform is added dropwise with stirring to a solution, cooled to 0° C., of 190 g (1.1 mol) of N-(3-fluorophenyl)-thiourea in 1100 ml of chloroform and the reaction mixture is then heated under reflux for 4 hours. It is then concentrated, the residue is taken up in 3 liters of water and the mixture is adjusted to pH=1 with conc. sulphuric acid. It is then filtered and the filtrate is rendered alkaline with conc. ammonia. The product, which is obtained in crystalline form, is isolated by filtering off with suction.

147 g (70% of theory) of 2-amino-5-fluoro-benzothiazole of melting point 167° C. are obtained.

Step 3

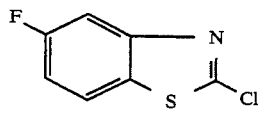

A solution of 242 g (3.5 mol) of sodium nitrite in 440 ml of water is added dropwise with stirring to a mixture, cooled to −10° C., of 147 g (0.87 mol) of 2-amino-5-fluoro-benzothiazole, 1700 ml of conc. hydrochloric acid and 20 g of copper power and the reaction mixture is stirred at 0° C. for 60 minutes and at 50° C. for a further 60 minutes. It is then extracted with chloroform and the solvent is carefully removed by distillation from the organic phase in a water-jet vacuum. 80 g (49% of theory) of 2-chloro-5-fluoro-benzothiazole are obtained as a crystalline residue of melting point 69° C.

Example (II-2)

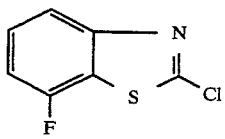

Step 1

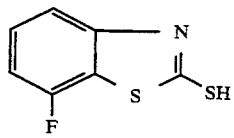

A mixture of 12.9 g (0.1 mol) of 2,3-difluoroaniline and 30 ml of dimethylformamide is heated to reflux and at the same time a solution of 48 g (0.3 mol) of potassium ethyl xanthate in 80 ml of dimethylformamide is added dropwise in the course of 1 hour. The bottom temperature is kept at 145° C. by removal of distillate. The reaction mixture is stirred under reflux for 15 hours and poured into 1 liter of water after cooling. It is then acidified at 10° C. with a solution of 20 ml of conc. hydrochloric acid in 30 ml of water and the crystalline product is isolated by filtering off with suction.

18.0 g (87% of theory) of 2-mercapto-7-fluoro-benzothiazole of melting point 193° C. are obtained.

Step 2

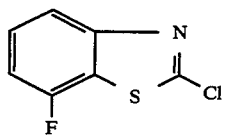

9.3 g (44.5 mmol) of 2-mercapto-7-fluoro-benzothiazole are added to 50 ml of thionyl chloride and, after addition of 1 ml of dimethylformamide, the mixture is slowly heated to reflux. After stirring under reflux for one hour, the mixture is cooled and concentrated in a water-jet vacuum. The residue is taken up in methylene chloride, washed with water, dried with sodium sulphate and filtered. The filtrate is concentrated and the residue is purified by column chromatography (silica gel/methylene chloride).

4.3 g (45% of theory) of 2-chloro-7-fluoro-benzothiazole are obtained as a yellow oil.

Example (II-3)

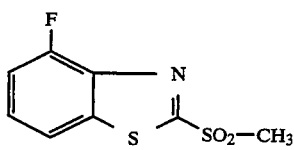

Step 1

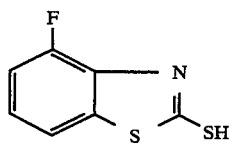

A mixture of 97 g (0.75 mol) of 2,6-difluoroaniline, 120 g (0.75 mol) of potassium ethyl xanthate and 750 ml of dimethyl sulphoxide is stirred at 120° C. for 3 hours. After cooling, it is diluted with 300 ml of water and adjusted to pH=1 with conc. hydrochloric acid. The product which is obtained in crystalline form in this way is isolated by filtering off with suction.

120 g (80% of theory) of 2-mercapto-4-fluoro-benzothiazole of melting point 180° C. are obtained.

Step 2

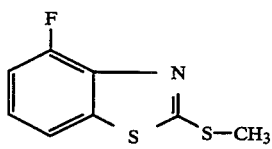

111 g (0.77 mol) of methyl iodide are added dropwise with stirring to a mixture, cooled to 0° C., of 120 g (0.65 mol) of 2-mercapto-4-fluoro-benzothiazole, 26 g (0.65 mol) of sodium hydroxide and 750 ml of water. The reaction mixture is stirred for 3 hours and the product, which is obtained in crystalline form, is isolated by filtering off with suction.

51 g (39% of theory) of 2-methylthio-4-fluoro-benzothiazole of melting point 30° C. are obtained.

Step 3

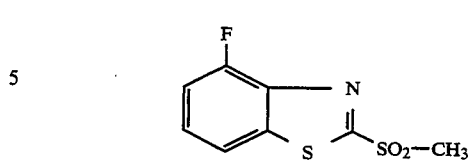

145 ml of a 35% strength aqueous hydrogen peroxide solution (1.7 mol of $H_2O_2$) are added dropwise with stirring to a mixture, kept at 30° C., of 51 g (0.25 mol) of 2-methylthio-4-fluoro-benzothiazole, 500 ml of chloroform, 25 ml of formic acid and 2.5 ml of conc. sulphuric acid and also 2 g of ammonium molybdate. The reaction mixture is stirred at 30° C. for 2 hours and the product, which is obtained in crystalline form, is isolated by filtering off with suction.

31 g (54% of theory) of 2-methylsulphonyl-4-fluorobenzothiazole of melting point 160° C. are obtained.

2-Methylsulphonyl-7-fluoro-benzothiazole of the formula below, for example, is also obtained analogously to Example (II-3) via 2-mercapto-7-fluoro-benzothiazole and 2-methylthio-7-fluoro-benzothiazole.

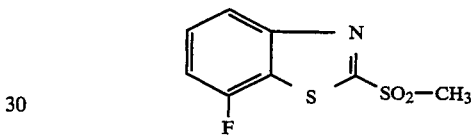

USE EXAMPLES

The compound shown below is used as a comparison substance in the following use examples:

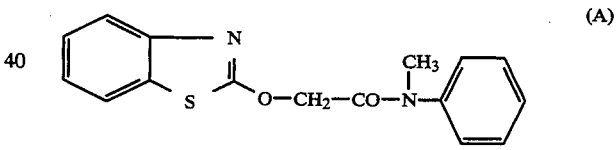

(A)

N-methylbenzothiazol-2-yl-oxyacetanilide (mefenacet) (disclosed in EP-A-5,501, Ex. 1)

Example A

Pre-emergence water surface treatment in transplanted paddy rice

To prepare an applicable preparation, 1 part of active compound is dissolved using 5 parts of acetone; 1 part of benzyloxy polyglycol ether is then added as an emulsifier. Water is then added to the desired concentration. Rice in the 2–3 leaf stage is transplanted into pots which are filled with soil. Seeds of test plants are sown (1 cm deep). Two days later, the pots are flooded with 3 cm of water. The active compound preparations are then applied to the water surface. 4 weeks later, the herbicidal action and the damage to the untreated plants is assessed visually in % in comparison to untreated plants. 0% denotes no effect, 100% denotes complete destruction.

In this test, the in part very good tolerability of the active compounds according to the invention—in particular the compounds from Preparation Examples (3), (4), (5), (6) and (7)—is seen in rice together with substantially more powerful action against weens in comparison with the known compound (A), in particular against barnyard grass (*Echinochloa crus galli*). The compound from Preparation Example (39) acts in the same way.

Example B

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, the compounds according to Preparation Examples (2), (4), (5), (6) and (7) show powerful action against weeds, together with good tolerability for crop plants, such as, for example, soya. Here again, compound (39) acts in analogous manner.

It will be appreciated that the instant specification and claims are set forth by way of illustration and not limitation, and that various modifications and changes may be made without departing from the spirit and scope of the present invention.

We claim:

1. A fluorobenzothiazolyloxyacetamide of the formula

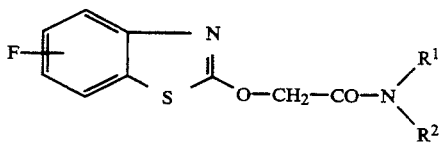

(I)

in which
- $R^1$ represents hydrogen or an optionally substituted radical from the group consisting of alkyl, alkenyl, alkinyl and aralkyl,
- $R^2$ represents an optionally substituted radical from the group consisting of alkyl, alkenyl, alkinyl, cycloalkyl, cycloalkenyl, aralkyl, aryl, alkoxy, alkenyloxy or alkinyloxy, or
- $R^1$ and $R^2$, together with the nitrogen atom to which they are bonded, form an optionally substituted, saturated or unsaturated nitrogen heterocycle which can contain further heteroatoms and to which a benzo group can be fused.

2. A compound according to claim 1, in which characterised in that, in these compounds
- $R^1$ represents hydrogen, $C_1$-$C_8$-alkyl (which is optionally substituted by fluorine, chlorine, cyano or $C_1$-$C_4$-alkoxy), $C_2$-$C_8$-alkenyl (which is optionally substituted by fluorine and/or chlorine), $C_2$-$C_8$-alkinyl or benzyl,
- $R^2$ represents $C_1$-$C_8$-alkyl (which is optionally substituted by fluorine, chlorine, cyano or $C_1$-$C_4$-alkoxy), $C_2$-$C_8$-alkenyl (which is optionally substituted by fluorine and/or chlorine), $C_2$-$C_8$-alkinyl, $C_3$-$C_6$-cycloalkyl (which is optionally substituted by chlorine and/or $C_1$-$C_3$-alkyl), $C_5$- or $C_6$-cycloalkenyl, benzyl (which is optionally substituted by fluorine, chlorine and/or $C_1$-$C_4$-alkyl), phenyl (which is optionally substituted by fluorine, chlorine, bromine, iodine, cyano, nitro, $C_1$-$C_4$-alkyl, trifluoromethyl, $C_1$-$C_4$-alkoxy and/or $C_1$-$C_4$-alkylthio), $C_1$-$C_8$-alkoxy (which is optionally substituted by $C_1$-$C_4$-alkoxy) or $C_3$-$C_4$-alkenyloxy, or
- $R^1$ and $R^2$, together with the nitrogen atom to which they are bonded, form an optionally saturated or unsaturated five- to seven-membered nitrogen heterocycle which is monosubstituted to trisubstituted by $C_1$-$C_3$-alkyl and optionally benzofused.

3. A compound according to claim 1, in which
- $R^1$ represents $C_1$-$C_4$-alkyl, allyl or propargyl,
- $R^2$ represents $C_1$-$C_6$-*alkyl*, $C_1$-$C_2$-alkoxy-$C_1$-$C_2$-alkyl, allyl, propargyl, cyclopentyl, cyclohexyl, cyclohexenyl, benzyl, phenyl (which is optionally substituted by fluorine, chlorine, bromine, cyano, nitro, methyl, ethyl, trifluoromethyl, methoxy or ethoxy), $C_1$-$C_6$-alkoxy or $C_1$-$C_2$-alkoxy-$C_1$-$C_2$-alkoxy, or
- $R^1$ and $R^2$, together with the nitrogen atom to which they are bonded, represent piperidinyl which is optionally monosubstituted to trisubstituted by methyl and/or ethyl, pyrrolidinyl which is optionally monosubstituted or disubstituted by methyl and/or ethyl, perhydroazepinyl or 1,2,3,4-tetrahydro(iso)quinolyl.

4. A 4-fluoro-, 5-fluoro-, 6-fluoro- or 7-fluorobenzothiazolyloxyacetamide of the formulas (IC), (ID), (IA) or (IB), respectively, according to claim 1:

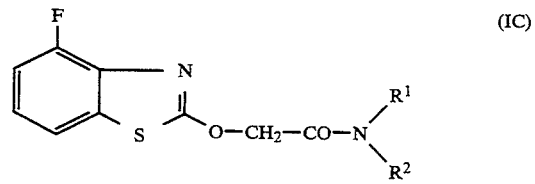

(IC)

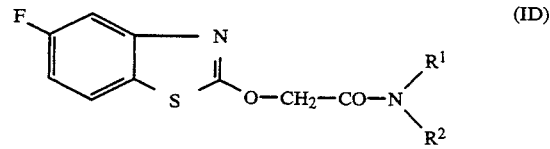

(ID)

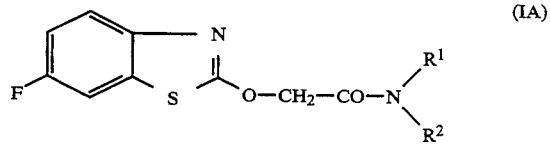

(IA)

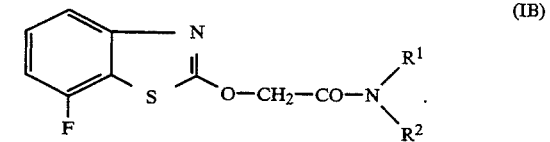

(IB)

5. A compound according to claim 1, wherein such compound is N-methyl-α-(7-fluoro-benzothiazol-2-yloxy)-acetanilide of the formula

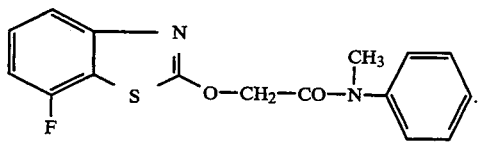
(2)

6. A compound according to claim 1, wherein such compound is N-methyl-N-(2,3-dimethyl-phenyl)-α-(5-fluoro-benzothiazol-2-yl-oxy)-acetamide of the formula

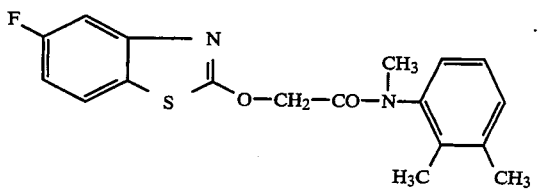
(3)

7. A compound according to claim 1, wherein such compound is N-isopropyl-N-(4-fluoro-phenyl)-α-(5-fluoro-benzothiazol-2-yl-oxy)-acetamide of the formula

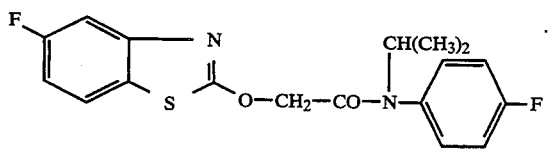
(4)

8. A compound according to claim 1, wherein such compound is N-isopropyl-α-(5-fluoro-benzothiazol-2-yl-oxy)acetanilide of the formula

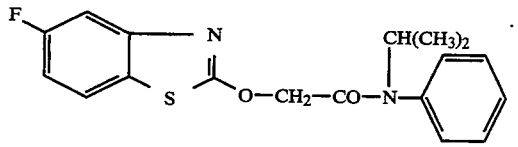
(5)

9. A compound according to claim 1, wherein such compound is N-methyl-N-(3-methyl-phenyl)-α-(5-fluoro-benzothiazol-2-yl-oxy)-acetamide of the formula

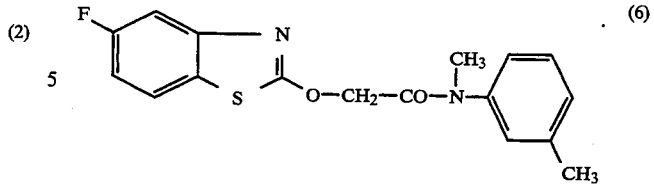
(6)

10. A compound according to claim 1, wherein such compound is N-methyl-N-(2-methyl-phenyl)-α-(5-fluoro-benzothiazol-2-yl-oxy)-acetamide of the formula

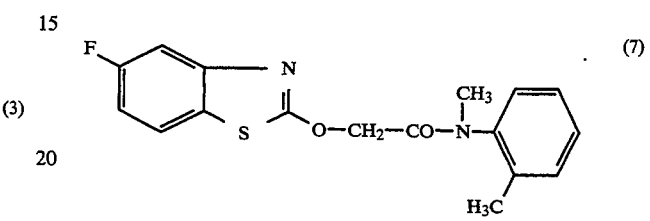
(7)

11. A compound according to claim 1, wherein such compound is N-isopropyl-N-(4-fluoro-phenyl)-α-(7-fluoro-benzothiazol-2-yl-oxy)-acetamide of the formula

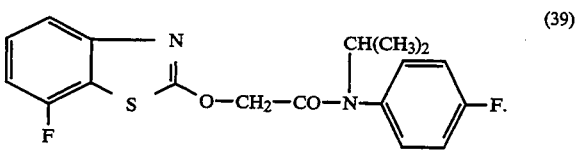
(39)

12. A herbicidal composition comprising a herbicidally effective amount of a compound according to claim 1 and a diluent.

13. A method of combating unwanted vegetation which comprises applying to such vegetation or to a locus from which it is desired to exclude such vegetation a herbicidally effective amount of a compound according to claim 1.

14. The method according to claim 13, wherein such compound is

N-methyl-α-(7-fluoro-benzothiazol-2-yl-oxy)-acetanilide,
N-methyl-N-(2,3-dimethyl-phenyl)-α-(5-fluoro-benzothiazol-2-yl-oxy)-acetamide,
N-isopropyl-N-(4-fluoro-phenyl)-α-(5-fluoro-benzothiazol-2-yl-oxy)-acetamide,
N-isopropyl-α-(5-fluoro-benzothiazol-2-yl-oxy)-acetanilide,
N-methyl-N-(3-methyl-phenyl)-α-(5-fluoro-benzothiazol-2-yl-oxy)-acetamide,
N-methyl-N-(2-methyl-phenyl)-α-(5-fluoro-benzothiazol-2-yl-oxy)-acetamide, or
N-isopropyl-N-(4-fluoro-phenyl)-α-(7-fluoro-benzothiazol-2-yl-oxy)-acetamide.

* * * * *

UNITED STATES PATENT AND TRADEMARK OFFICE
CERTIFICATE OF CORRECTION

PATENT NO. : 5,356,864
DATED : October 18, 1994
INVENTOR(S) : Forster, et al.

It is certified that error appears in the above-indentified patent and that said Letters Patent is hereby corrected as shown below:

Col. 30, line 21  Delete " $C_1-C_6$-alkyl " and substitute -- $C_1-C_6$-alkyl --, delete " $C_1-C_2$-alkoxy " and substitute -- $C_1-C_2$-alkoxy --

Signed and Sealed this

Seventh Day of May, 1996

Attest:

BRUCE LEHMAN

Attesting Officer

Commissioner of Patents and Trademarks